United States Patent
Kurtzberg et al.

(10) Patent No.: US 6,487,520 B1
(45) Date of Patent: Nov. 26, 2002

(54) DATA MINING TECHNIQUES FOR ENHANCING MEDICAL EVALUATION

(75) Inventors: Jerome M. Kurtzberg, Yorktown Heights, NY (US); Menachem Levanoni, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/449,138

(22) Filed: Nov. 24, 1999

(51) Int. Cl.$^7$ .............................................. G06F 15/00
(52) U.S. Cl. ...................................... 702/183; 600/300
(58) Field of Search ................................. 702/179, 183, 702/184; 707/200, 102, 3, 4; 600/300

(56) References Cited

U.S. PATENT DOCUMENTS

| | | | |
|---|---|---|---|
| 5,642,936 A | * | 7/1997 | Evans ......................... 600/300 |
| 5,908,383 A | * | 6/1999 | Brynjestad ................... 600/300 |
| 6,267,722 B1 | * | 7/2001 | Anderson et al. ........... 600/300 |

* cited by examiner

Primary Examiner—Marc S. Hoff
Assistant Examiner—Mohamed Charioui
(74) Attorney, Agent, or Firm—Stephen C. Kaufman, Esq.; McGinn & Gibb, PLLC

(57) ABSTRACT

A computer method for enhancing medical evaluation. The method includes the steps of providing a problem database comprising a compendium of patient medical history; providing a remedy database comprising a compendium of at least one of medical therapies, pharmaceuticals, medical information and medical diagnostics; and employing a data mining technique for interrogating the problem and remedy databases for generating an output data stream, the output data stream correlating patient problem with patient remedy.

4 Claims, 4 Drawing Sheets

DATA MINING TECHNIQUES FOR ENHANCING MEDICAL EVALUATION

BACKGROUND OF THE INVENTION

FIELD OF THE INVENTION

This invention relates to methodology for utilizing data mining techniques in the area of medical evaluation.

INTRODUCTION OF THE INVENTION

Data mining techniques are known and include disparate technologies, like neural networks, which can work to an end of efficiently discovering valuable, non-obvious information from a large collection of data. The data, in turn, may arise in fields ranging from e.g., marketing, finance, manufacturing, or retail.

SUMMARY OF THE INVENTION

We have now discovered novel methodology for exploiting the advantages inherent generally in data mining technologies, in the particular field of health and medical applications.

Our work proceeds in the following way.

We have recognized that a typical and important "three-part" paradigm for presently effecting medical evaluation, is a largely subjective, human paradigm, and therefore exposed to all the vagaries and deficiencies otherwise attendant on human procedures. In particular, the three-part paradigm we have in mind works in the following way. First, a doctor develops a problem database comprising a compendium of individual patient history—e.g., the patient's response to blood tests, x-rays, or the doctor's observations. Secondly, and independently, the doctor develops in his mind a remedy database comprising the doctor's personal, partial, and subjective knowledge of objective medical facts culled from e.g., the medical literature, the pharmaceutical literature, or input from colleagues or salespersons. Thirdly, the doctor subjectively correlates in his mind the necessarily incomplete and partial remedy database, with the patient problem database, in order to promulgate an individual's patient's prescribed medical evaluation and cure.

This three-part paradigm is part science and part art, and captures one aspect of the special genius of medicine. However, as suggested above, it is manifestly a subjective paradigm, and therefore open to human vagaries.

We now disclose a novel computer method which can preserve the advantages inherent in this three-part paradigm, while minimizing the incompleteness and attendant subjectivities that otherwise inure in a technique heretofore entirely reserved for human realization.

To this end, in a first aspect of the present invention, we disclose a novel computer method comprising the steps of:

i) providing a problem data base comprising a compendium of patient medical history;

ii) providing a remedy database comprising a compendium of at least one of medical therapies, pharmaceuticals, medical information and medical diagnostics; and iii) employing a data mining technique for interrogating said problem and remedy databases for generating an output data stream, said output data stream correlating patient problem with patient remedy.

The novel method preferably comprises a further step of updating the step i) problem database, so that it can cumulatively track the patient's medical history as it develops over time. For example, this step i) of updating the problem database may include the results of employing the step iii) data mining technique. Also, the method may comprise a step of refining an employed data mining technique in cognizance of pattern changes embedded in each database as a consequence of remedy results and updating the problem database.

The novel method preferably comprises a further step of updating the step ii) remedy database, so that it can cumulatively track an ever increasing and developing technical medical literature. For example, this step ii) of updating the remedy database may include the effects of employing a data mining technique on the problem database. Also, the method may comprise a step of refining an employed data mining technique in cognizance of pattern changes embedded in each database as a consequence of remedy results and updating the remedy database.

The novel method may employ advantageously a wide array of step iii) data mining techniques for interrogating the problem and remedy database for generating an output data stream, which output data stream correlates patient problem with patient remedy. For example, the data mining technique may comprise inter alia employment of the following functions for producing output data: classification-neural, classification-tree, clustering-demographic, clustering-neural, factor analysis, or principal component analysis, or expert systems.

In a second aspect of the present invention, we disclose a program storage device readable by machine to perform method steps for providing an interactive medical database, the method comprising the steps of:

i) providing a problem database comprising a compendium of patient medical history;

ii) providing a remedy database comprising a compendium of at least one of medical therapies, pharmaceuticals, medical information and medical diagnostics; and iii) employing a data mining technique for interrogating said problem and remedy databases for generating an output data stream, said output data stream correlating patient problem with patient remedy.

In a third aspect of the present invention, we disclose a computer comprising:

i) means for inputting a problem database comprising a compendium of patient medical history;

ii) means for inputting a remedy database comprising a compendium of at least one of medical therapies, pharmaceuticals, medical information and medical diagnostics;

iii) means for employing a data mining technique for interrogating said remedy databases; and iv) means for generating an output data stream, said output data stream correlating patient problem with patient remedy.

BRIEF DESCRIPTION OF THE DRAWING

The invention is illustrated in the accompanying drawing, in which.

DETAILED DESCRIPTION OF THE PRESENT INVENTION

The detailed description of the present invention proceeds by tracing through three quintessential method steps, summarized above, that fairly capture the invention in all its sundry aspects. To this end, attention is directed to the flowcharts and neural networks of FIGS. 1 through 4, which can provide enablement of the three method steps.

Figure 1:
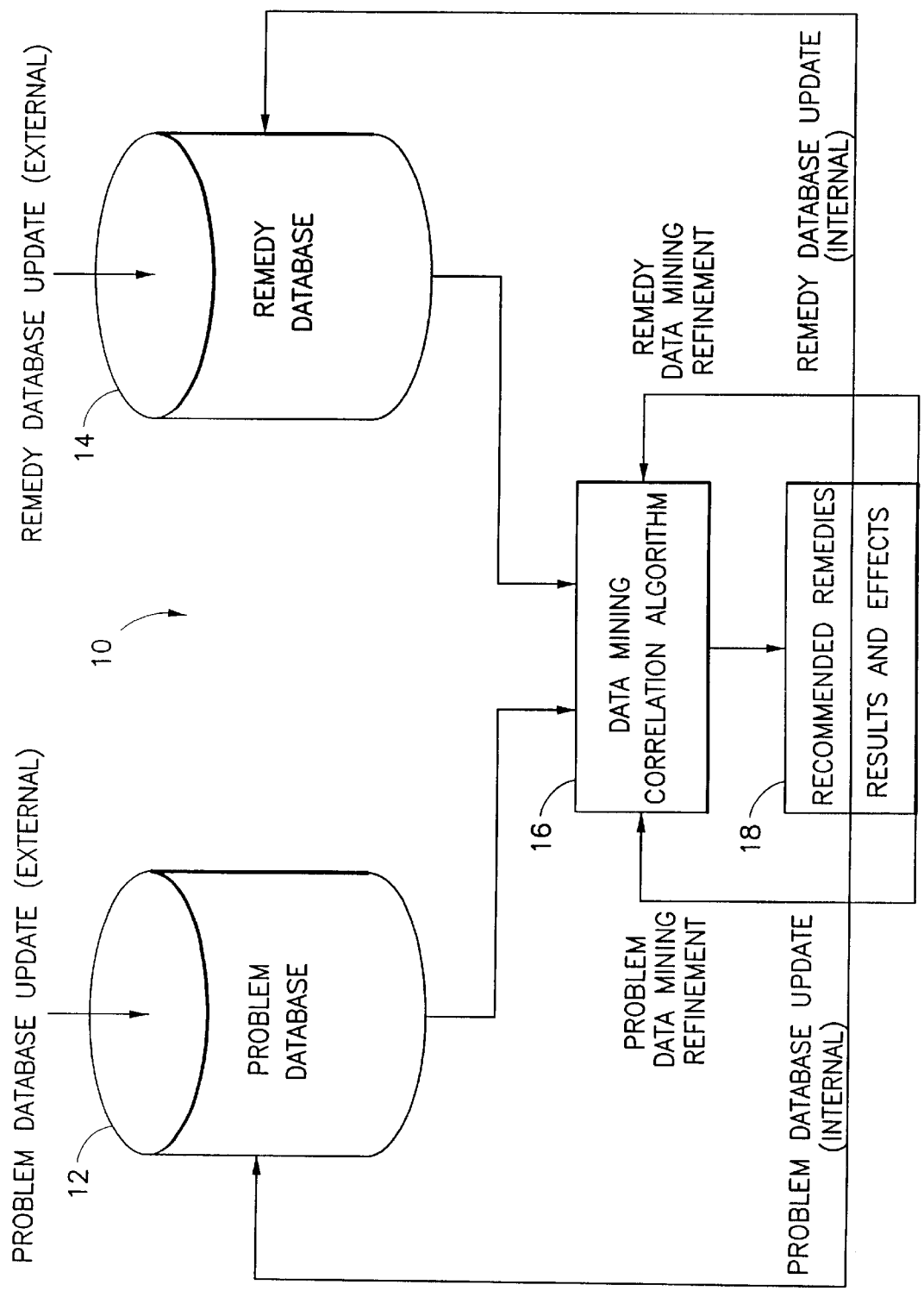
FIG. 1 provides an illustrative flowchart comprehending overall realization of the method of the present invention.

FIG. 1, numerals 10–18, illustratively captures the overall spirit of the present invention. In particular, the FIG. 1 flowchart (10) shows a problem database (12) comprising a compendium of patient medical history, and a remedy database (14) comprising a compendium of at least one of medical therapies, pharmaceuticals, medical information, and medical diagnostics. Those skilled in the art will have no difficulty, having regard to their own knowledge and this disclosure, in creating or updating the databases (12,14) e.g., conventional techniques can be used to this end. FIG. 1 also shows the outputs of the problem database (12) and remedy database (14) input to a data mining condition algorithm box (16). The data mining algorithm can interrogate the information captured and/or updated in the problem and remedy databases (12,14), and can generate an output data stream (18) correlating patient problem with patient remedy. Note that the output (18) of the data mining algorithm can be most advantageously, self-reflexively, fed as a subsequent input to at least one of the problem database (12), the remedy database (14), and the data mining correlation algorithm (16).

Figure 2:
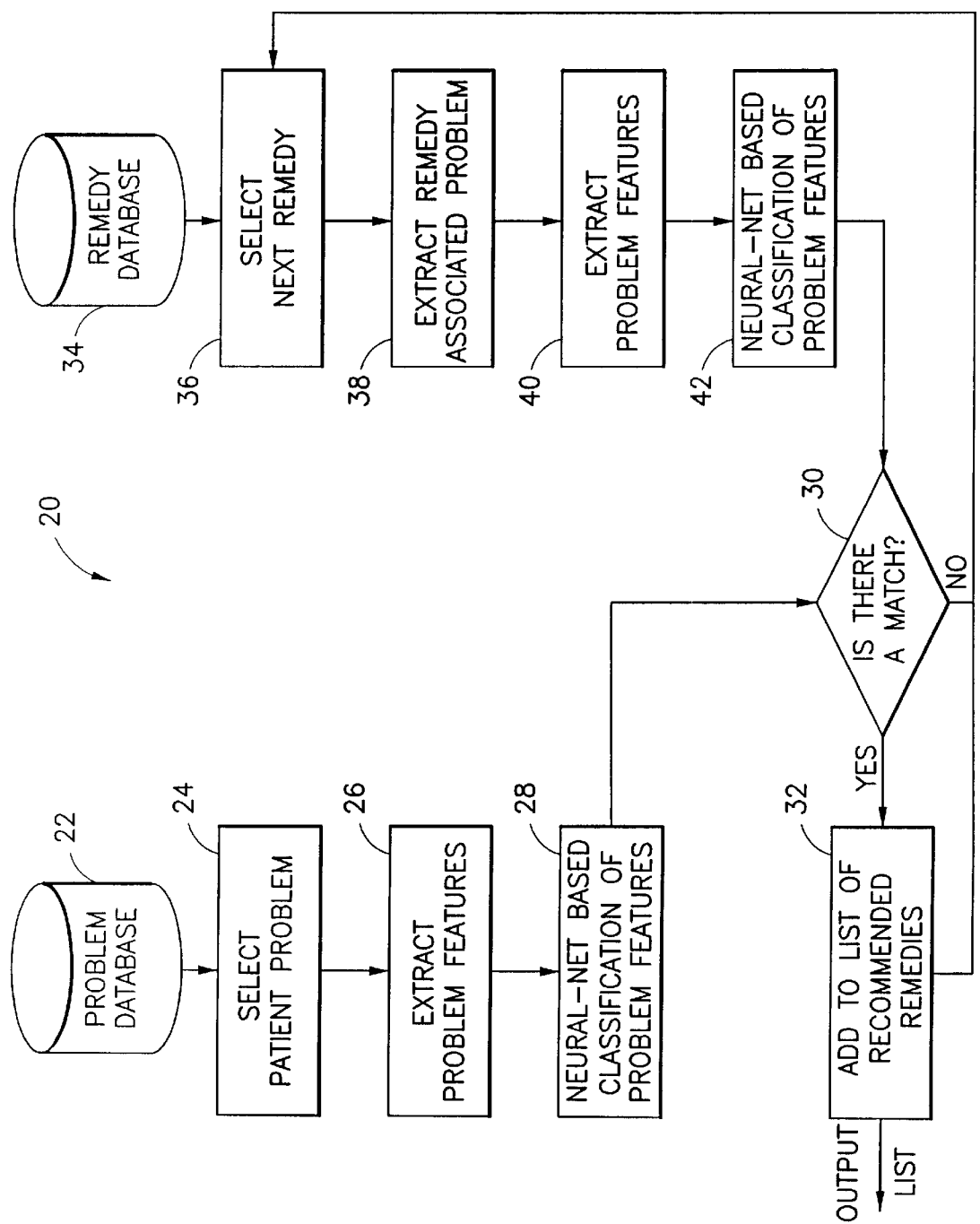
FIG. 2 provides an illustrative flowchart of details comprehended in the FIG. 1 flowchart.

Attention is now directed to FIG. 2, which provides a flowchart (20–42) that recapitulates some of the FIG. 1 flowchart information, but adds particulars on the immediate correlation functionalities required of a data mining correlation algorithm. For illustrative purposes, FIG. 2 comprehends the data mining correlation algorithm as a neural-net based classification of problem features, e.g., wherein a problem feature for say, prostate cancer, may include PSA, temperature, size of prostate, etc.

Figure 3:
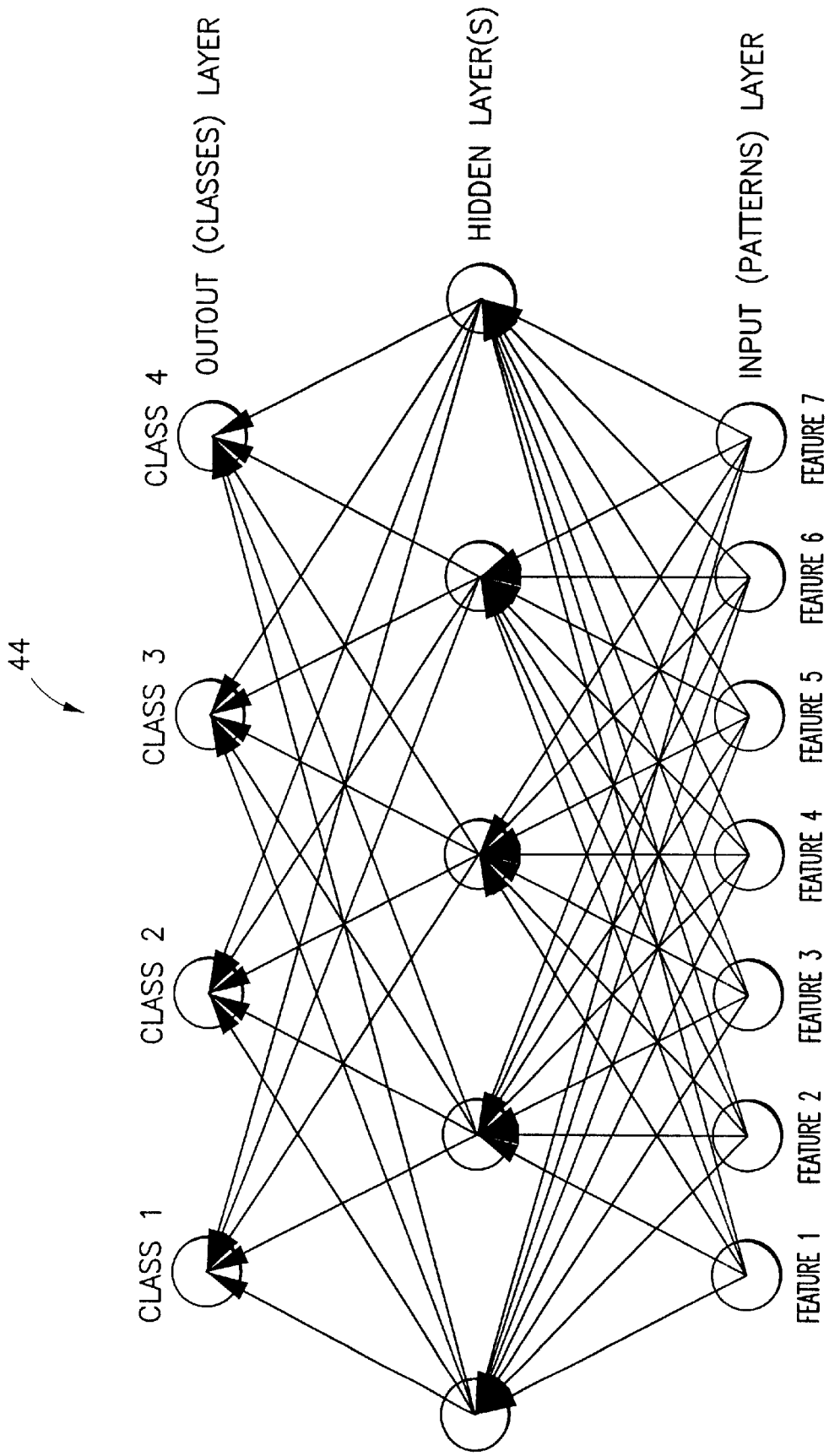
FIG. 3 shows a neural network that may be used in realization of the FIGS. 1 and 2 data mining algorithm.
Figure 4:
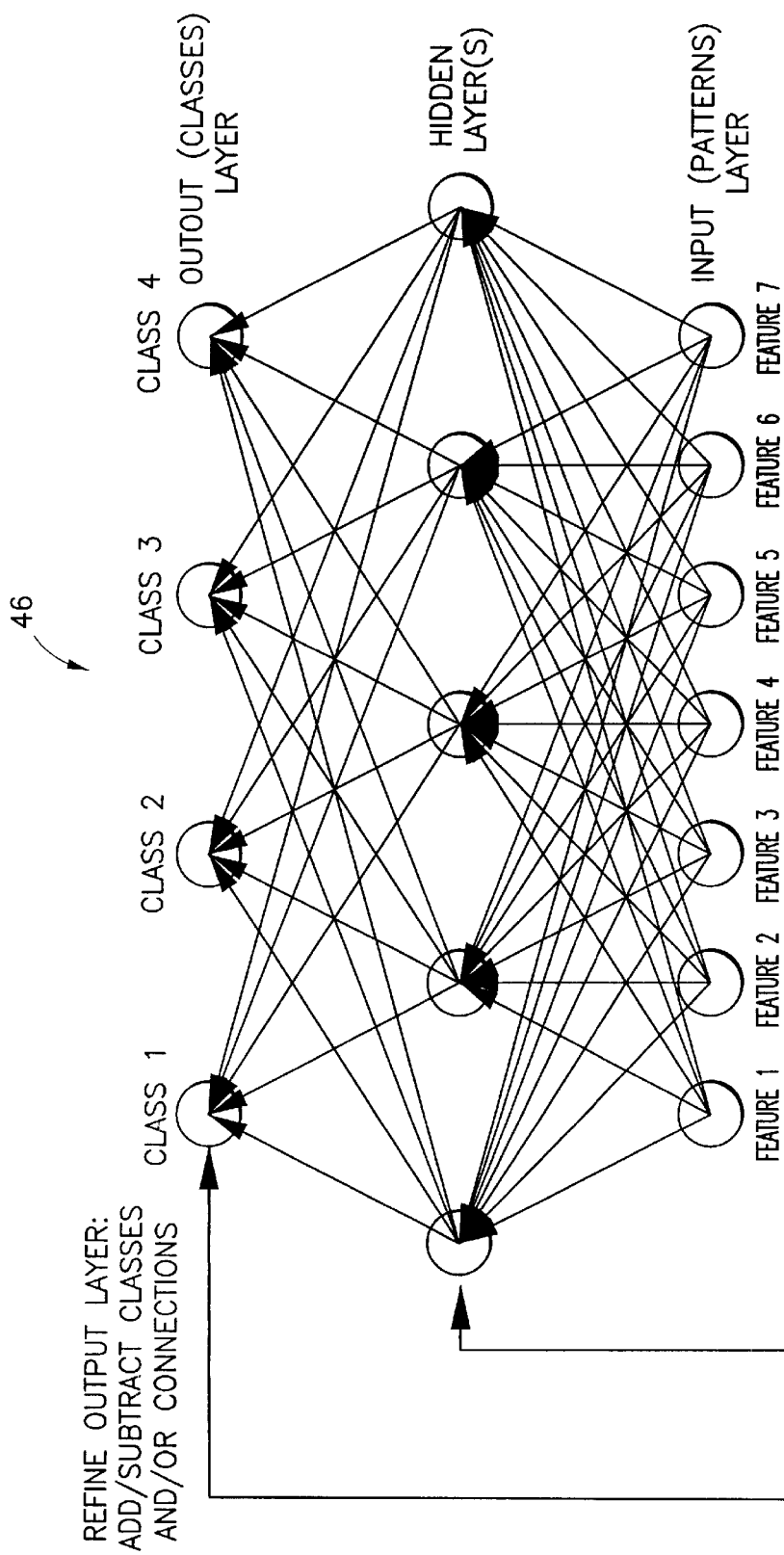
FIG. 4 shows further illustrative refinements of the FIG. 3 neural network.

FIG. 3, in turn, shows a neural-net (44) that may be used in realization of the FIGS. 1 and 2 data mining correlation algorithm. Note the reference to classes which represent classification of input features. The FIG. 3 neural-net (44) in turn, may be advantageously refined, as shown in the FIG. 4 neural-net (46), to capture the self-reflexive capabilities of the present invention, as elaborated above.

What is claimed:

1. A computer method comprising:

providing a problem database comprising a compendium of patient medical history;

providing a remedy database comprising a compendium of at least one of medical therapies, pharmaceuticals, medical information and medical diagnostics;

employing a data mining technique for interrogating said problem and remedy databases for generating an output data stream, said output data stream correlating a patient problem with a patient remedy;

updating the problem database; and refining an employed data mining technique in cognizance of pattern changes embedded in each database as a consequence of updating the problem database.

2. A computer method comprising:

providing a problem database comprising a compendium of patient medical history;

providing a remedy database comprising a compendium of at least one of medical therapies, pharmaceuticals, medical information and medical diagnostics;

employing a data mining technique for interrogating said problem and remedy databases for generating an output data stream, said output data stream correlating patient problem with patient remedy;

updating the remedy database; and refining an employed data mining technique in cognizance of pattern changes embedded in each database as a consequence of updating the remedy database.

3. A computer program storage, the program comprising:

instructions for providing a problem database comprising a compendium of patient medical history;

instructions for providing a remedy database comprising a compendium of at least one of medical therapies, pharmaceuticals, medical information and medical diagnostics;

instructions for employing a data mining technique for interrogating said problem and remedy databases for generating an output data stream, said output data stream correlating patient problem with patient remedy;

instructions for updating the problem database; and instructions for refining an employed data mining technique in cognizance of pattern changes embedded in each database as a consequence of updating the problem database.

4. A computer program storage, the program comprising:

instructions for providing a problem database comprising a compendium of patient medical history;

instructions for providing a remedy database comprising a compendium of at least one of medical therapies, pharmaceuticals, medical information and medical diagnostics;

instructions for employing a data mining technique for interrogating said problem and remedy databases for generating an output data stream, said output data stream correlating patient problem with patient remedy;

instructions for updating the remedy database; and instructions for refining an employed data mining technique in cognizance of pattern changes embedded in each database as a consequence of updating the remedy database.

* * * * *